United States Patent [19]
Kamphoefner et al.

[11] 3,988,934
[45] Nov. 2, 1976

[54] HANDWRITING SENSING AND ANALYZING APPARATUS

[75] Inventors: Fred J. Kamphoefner, Atherton; Gerry B. Andeen, Menlo Park, both of Calif.

[73] Assignee: Stanford Research Institute, Menlo Park, Calif.

[22] Filed: Jan. 5, 1976

[21] Appl. No.: 646,657

[52] U.S. Cl. ............................ 73/432 R; 73/133 R; 338/2; 338/5
[51] Int. Cl.² ........................................... G01L 5/16
[58] Field of Search ............. 73/133 R, 172, 432 R, 73/65; 128/2 N, 2 S; 338/2, 5, 6

[56] References Cited
UNITED STATES PATENTS

| | | | |
|---|---|---|---|
| 2,814,946 | 12/1957 | Harris, Jr. | 338/5 X |
| 3,563,097 | 2/1971 | Roggenstein et al. | 73/432 R |
| 3,894,437 | 7/1975 | Hagy et al. | 73/432 R |

Primary Examiner—Richard C. Queisser
Assistant Examiner—John S. Appleman
Attorney, Agent, or Firm—Lindenberg, Freilich, Wasserman, Rosen & Fernandez

[57] ABSTRACT

A compact apparatus for analyzing a signature or other handwritten markings, including a horizontal platen which can support paper on which a signature is written, a pair of inner beams extending horizontally from opposite sides of the platen to an intermediate structure, and a pair of outer beams extending horizontally, and in directions perpendicular to the inner beams, between the intermediate structure and a supporting frame. Strain gauges are attached to the sides of the inner and outer beams to sense forces applied to the platen by the tip of a writing instrument in the horizontal "X" and "Y" directions, and additional strain gauges are attached to opposite faces of the outer beams to sense forces in the vertical, or "Z," direction.

11 Claims, 10 Drawing Figures

HANDWRITING SENSING AND ANALYZING APPARATUS

BACKGROUND OF THE INVENTION

This invention relates to apparatus which generates signals representing the force and direction of motion of the tip of a writing instrument.

The analysis of handwriting, as in verifying signatures, can be accomplished by sensing the forces applied by the pen or pencil used to write the signature. The sensors can be located in either the writing instrument or in the table-like structure that supports the paper on which the signature is written. For example, a patent application for "Strain Gauge Transducer System" by Crane et al., Ser. No. 451,846 filed Mar. 15, 1975, and assigned to the assignee of the present application, describes the use of strain gauges contained in a small writing instrument to sense the force applied by the pen and the directions of motion of the pen, as a signature is written. As another example, U.S. Pat. No. 3,563,097 shows a device for sensing downward force of a writing instrument on a tablet of a table-like apparatus. In many situations, a table-like structure is desirable, because it avoids the need for wires to extend to the writing instrument. However, previous table-like apparatus has been relatively bulky, and also has sensed only simple downward force of the writing instrument.

SUMMARY OF THE INVENTION

In accordance with one embodiment of the present invention, a handwriting analyzing apparatus is provided which is compact, simple, and rugged. The apparatus includes a platen with a horizontal support surface for supporting a sheet of paper on which a signature or other handwriting is to be written. The platen is supported by a pair of horizontally-extending inner beams. Strain gauges coupled to the beams sense the deflection thereof to thereby sense forces applied by the tip of a writing instrument to the platen.

In order to permit the sensing of forces in multiple directions, the inner beams are supported by an intermediate structure that surrounds the platen, and the intermediate structures is, in turn, supported by a pair of outer beams which are attached to a frame. The outer beams extend horizontally but in directions perpendicular to the inner beams. Thus, strain gauges attached to the sides of the inner beams measure forces in the X direction, while strain gauges attached to the sides of the outer beams measure the forces in the Y direction. Additional strain gauges are attached to the upper and lower faces of one pair of beams to additionally sense forces in the Z, or vertical, direction.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
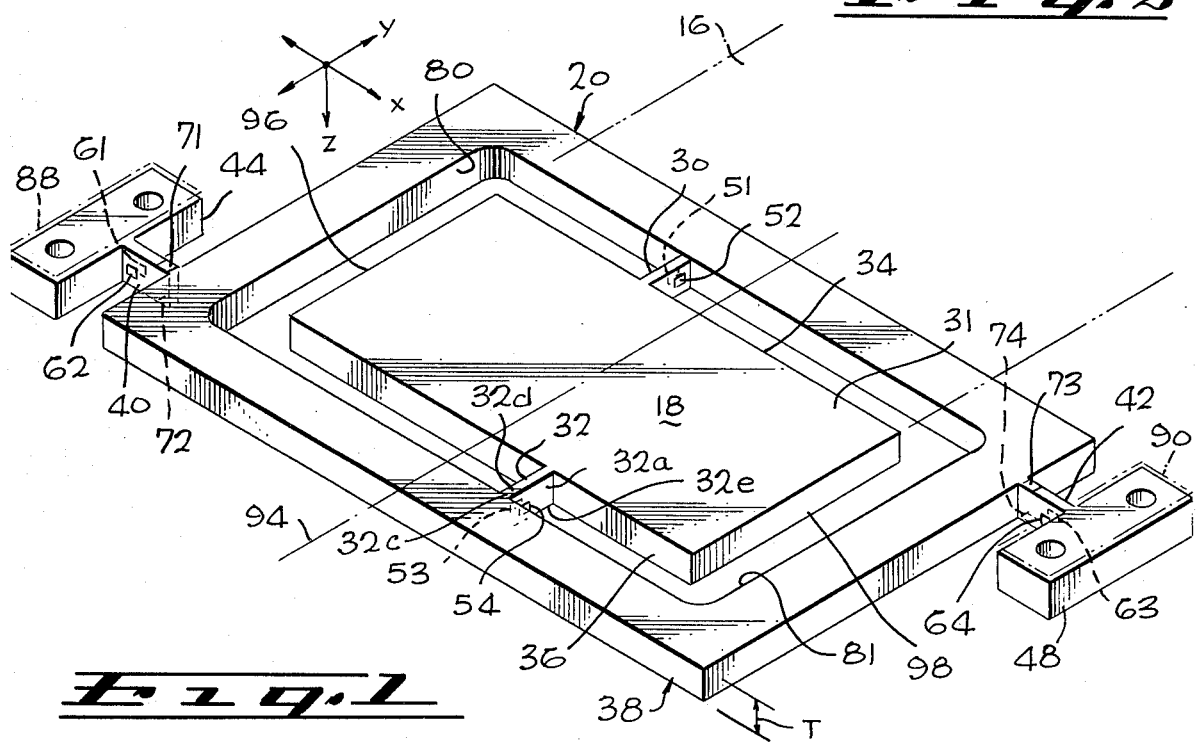
FIG. 1 is a perspective top view of a handwriting analyzing apparatus constructed in accordance with the present invention.

FIG. 1 illustrates handwriting analyzing apparatus 10 which includes a frame 12 on which a person rests his hand H while holding a writing instrument 14 such as an ordinary pen or pencil. The apparatus also includes a sheet of paper 16 on which a signature or other handwriting is written, and a tablet or platen 18 which supports the paper in good frictional engagement therewith, to receive forces applied by the tip of the writing instrument. The platen 18 is part of a writing sensor 20 which generates signals determined by the forces applied by the tip of the writing instrument.

The output of the writing sensor 20 is delivered to an analyzing circuit 22 which analyzes the handwriting. The circuit 22 can be constructed to determine the forces applied in one, two, or three orthogonal directions, and to measure the variations of these forces with time and/or the variation of the these forces with respect to one another. In one application, the authenticity of a signature can be determined by comparing the force-time variations of the signature with those of a previously verified signature. In another application, described in U.S. Patent application Ser. No. 438,413 filed Jan. 31, 1974, now 3,930,229, the forces are analyzed to determine the particular character which has been written.

Figure 2:
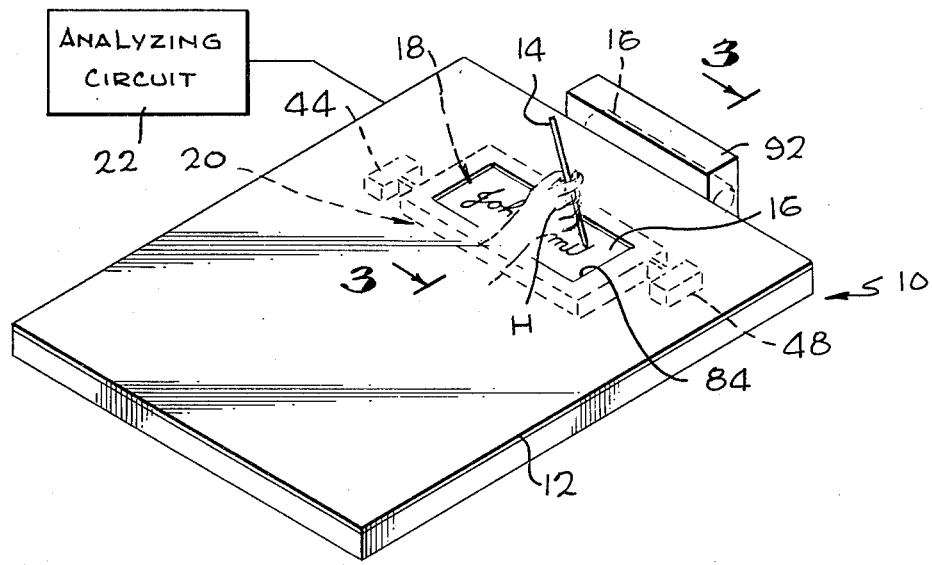
FIG. 2 is a partial top perspective view of the apparatus of FIG. 1.
Figure 3:
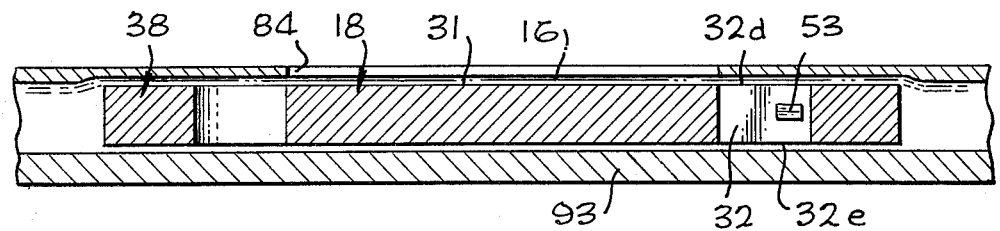
FIG. 3 is a view taken on the line 3—3 of FIG. 1.

FIG. 2 illustrates details of the writing sensor 20 which senses the forces applied by the tip of a writing instrument to a portion of a paper sheet 16 which lies over a platen 18. The platen 18 has a substantially horizontally-extending upper surface 31 which supports the forces produced by the tip of the writing instrument. The platen 18 is connected by a pair of inner beams 30, 32 which extend in a substantially horizontal direction from opposite sides 34, 36 of the platen. Each of the inner beams extends to a rigid intermediate structure 38 which extends around the platen. The intermediate structure 38 is, in turn, supported by a pair of outer beams 40, 42 that extend in a substantially horizontal direction from the intermediate structure to a pair of anchor pads 44, 48 which are fixed to the frame 12.

The writing sensor 20 is designed to sense forces in three orthogonal directions as indicated by the arrows X, Y, and Z. Forces applied in the X direction cause bending of the inner beams 30, 32. Four strain gauges 51, 52, 53, and 54 are applied to the sides of the inner beams 30, 32. The resistances of these strain gauges vary according to bending of the inner beams, which varies in accordance with the forces applied by the tip of the writing instrument in the X direction. In a similar manner, four strain gauges 61, 62, 63, and 64 are applied to the sides of the outer beams 40, 42, to sense deflection of these beams, and therefore to sense the force applied in the Y direction by a writing instrument to the paper which is supported by the platen 18. In order to measure forces in the Z direction, or in other words, the force with which the tip of the writing instrument presses towards the platen, four additional strain gauges 71, 72, 73, 74 are utilized, which are applied to the upper and lower faces of each of the outer beams 40, 42. Of course, the gauges 71 - 74 could, instead be applied to the inner beams.

The writing sensor 20 can be formed from a single plate of material such as 6061 T6 aluminum. A pair of U-shaped slots 80, 81 can be formed in the plate, with the ends of the legs of the U's spaced a small distance from one another to leave the inner beams 30, 32. The slots also form the platen 18 and separate it from the surrounding intermediate structure 38. The peripheral portion of the plate can also be cut away to leave the outer beams 40, 42 and the anchor pads 44, 48. In one writing sensor 20, that has been constructed having the form shown in FIG. 2, a plate with a thickness T of one-quarter inch was utilized to form a writing sensor with a platen 18 having a length of three and one-quarter inches, and with inner and outer beams 30, 32, 40, 42 of a width of one-sixteenth inch and a length of one-half inch. It can be appreciated that the writing sensor 20 is relatively rugged and is compact, especially in the thickness or Z direction.

The frame 12 (FIG. 1) on which the hand of a person rests, may be formed as a sheet with a hole 84 which surrounds the platen 18. Where the frame 12 is thin, the paper 16 can lie directly on the platen without the level of the paper being considerably below the level of the frame 12. However, if desired, a pad can be placed over the platen to raise the level of the paper to the same level as the upper surface of the frame. The anchor pads 44, 48 are fastened to the lower surface of the sheet-like frame 12, by utilizing shims 88, 90 to leave a slight separation between the writing sensor 20 and frame so that the platen 18, intermediate structure 38, and beams are unimpeded in slight horizontal and vertical movement. The pads 44, 48 are also fixed to a base plate 93. The paper 16 can be fed in any direction over the platen, as from a roll in a container 92. It is also possible to have persons write directly on a variety of devices which permit rapid erasing or other manner of removal of a signature.

Each of the strain gauges 51–54 and 61–64 which sense horizontal forces, are preferably positioned near one end of a beam and at a location halfway between the opposite faces of the beam. For example, strain gauge 54 is applied to a side 32a of the beam 32 near one end 32c of the beam. Also, the gauge 54 is applied halfway between the upper face 32d and lower face 32e of the beam. The application of the strain gauge near one end 32c of the beam results in maximum sensitivity, inasmuch as the greatest bending occurs near the ends of the beam. The application of the strain gauge halfway between the upper and lower faces 32d, 32e, results in greater isolation of the gauges from forces which tend to twist the beam.

It may be noted that the two inner beams 30, 32 do not extend from the middle of the platen. Instead these beams extend from locations along the sides 34, 36 of the platen which are spaced on opposite sides of an imaginary lateral line 94 that lies halfway between the opposite ends 96, 98 of the platen. This placement of the beams results in their being less affected by torque resulting from the application of forces by the writing instrument tip when the tip is located near either end 96, 98 of the platen.

Figure 4:
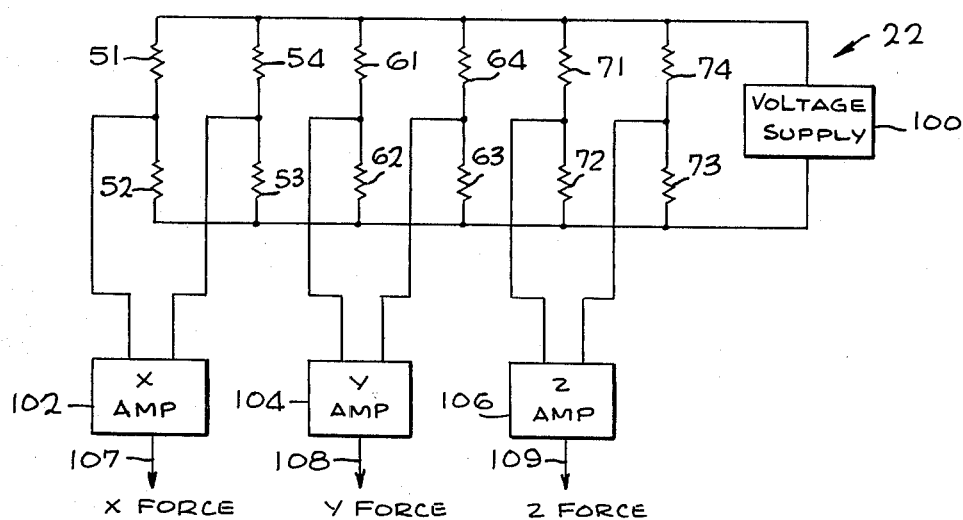
FIG. 4 is a circuit diagram showing a portion of the analyzing circuit of the apparatus of FIG. 1.

FIG. 4 illustrates a portion of the analyzing circuit 22 which is utilized to sense forces applied to the platen in each of three orthogonal directions, in a manner that substantially cancels out torques. Of course, it would be possible to minimize torques by utilizing four inner beams located at the opposite ends of the platen at either side thereof. However, a greater number of beams would result in greater manufacturing costs and the need to utilize thinner beams to achieve the same sensitivity. The four strain gauges 51–54 of FIG. 4, with two gauges on each beam, also results in good temperature compensation. The same advantages are obtained for each of the other sets of gauges 61–64 and 71–74. The bridge circuitry of FIG. 4 utilizes a voltage supply 100 which is applied in parallel to six pairs of the strain gauges, and includes three amplifiers 102, 104, 106, that amplify the differences in resistance changes or voltage changes across the strain gauges resulting from beam deflections, to obtain output signals on lines 107, 108, and 109 proportional to forces in the X, Y, and Z directions.

Figure 5:
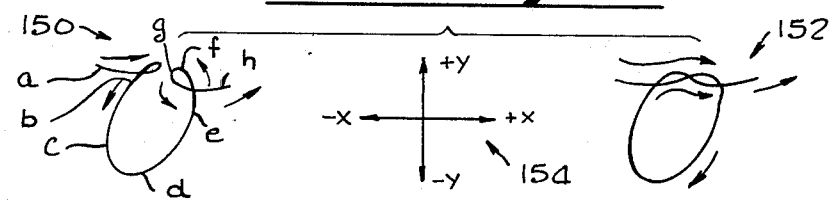
FIG. 5 is a representation of handwritings of the letter "o"
Figure 6:
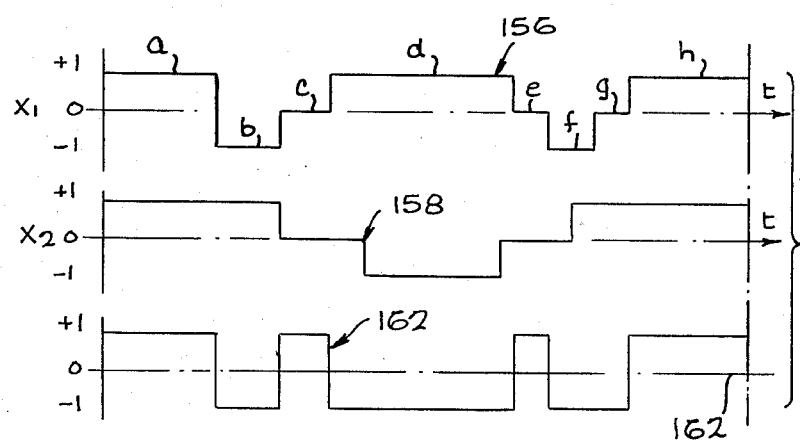
FIG. 6 is a set of graphs indicating the characteristics of the different ways in which the letters of FIG. 5 are written.

An example of one way in which the writing sensor of FIG. 2 can be utilized to verify a signature is explained below, in conjunction with FIGS. 5–7. FIG. 5 illustrates two ways in which a person may write the letter "o," with the writings producing letters 150 and 152 of similar appearance. The directions X and Y are indicated by the arrows 154. FIG. 6 has two graphs 156, 158 which show the directions, along the X axis, in which the writing instrument has moved during the writing of each letter 150, 152. In writing the letter 150, the writing instrument moves forward in the X direction along the portion $a$, then moves rearwardly in the X direction along the portion $b$, then does not move with any X directional component along the portion $c$, etc. The corresponding graph 156 provides a "+1" along the graph portion $a$ to indicate movement in the forward X direction during the $a$ portion of the letter 150, then provides "−1" along the graph portion $b$ to indicate movement in the rearward X direction, then provides a "o" along the graph portion $c$ to indicate no X directional component, etc. The horizontal ordinate "$t$" in the graph 156 represents the time occupied by each portion of the graph as a percent of the entire time required to write the letter "o". The graph 158 similarly indicates the directions of the writing instrument while writing the letter 152.

The two graphs 156, 158 can be compared, point by point, to determine their degree of correspondence. A comparison graph 160 indicates the correspondence of the graphs 156, 158, with a +1 on graph 160 indicating both graphs 156, 158, are identical (both −1, or both +1, or both "o"), while a −1 on graph 160 indicates a lack of correspondence. The average value 162 of graph 160 is about zero, which indicates a low degree of correspondence of the graphs 156, 158, and therefore indicates that the letters were written differently.

Figure 7:
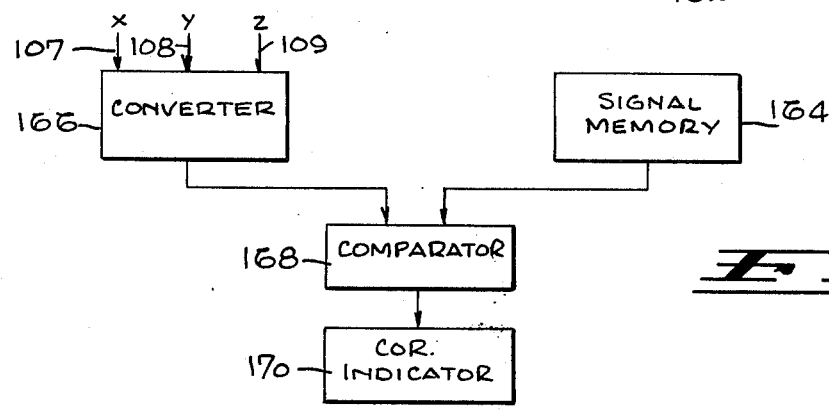
FIG. 7 is a simplified block diagram of a comparing circuit for providing the type of comparison indicated by the graphs of FIG. 6.

FIG. 7 is a simplified block diagram showing how two signatures are compared. Memory 164 contains information corresponding to graph 156, which indicates the direction of movement of a writing instrument along the X axis at any given time, during the writing of a verified signature. Information corresponding to graph 158, which indicates the direction of movement of a writing instrument along the X axis is received by a converter 166 over line 107. The converter 166 includes threshold detectors that assign the values +1, 0, or −1 to each incoming signal. The outputs of the two circuits are compared by a comparator 168, which generates an output delivered to an indicator 170 that indicates the degree of correspondence of the two signatures. A similar comparison is made for forces in the Y and Z directions. The above is a simplified comparison, which is effective only if a person writes his signature very much in the same way at all times. A more sophisticated comparison technique is required where there is considerable variation in the manner in which a person writes his signature.

Figure 8:
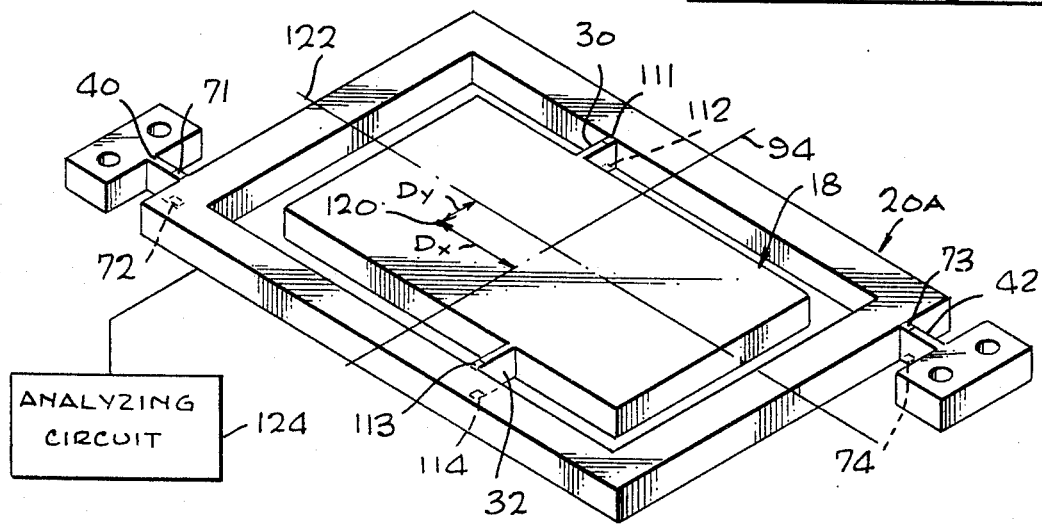
FIG. 8 is a partial perspective view of handwriting analyzing apparatus constructed in accordance with another embodiment of the invention.
Figure 9:
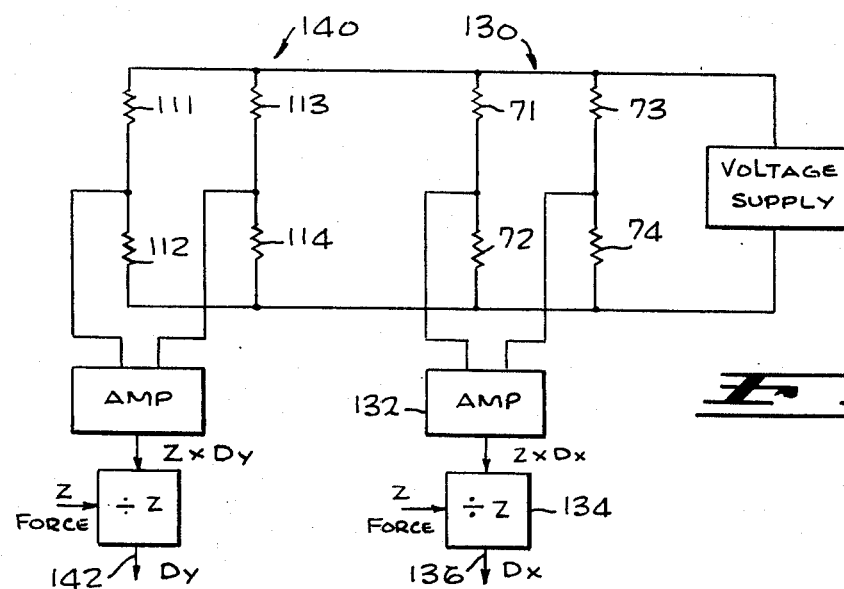
FIG. 9 is a circuit diagram showing a portion of the analyzing circuit of the apparatus of FIG. 8.

Although the measurement of forces in up to three orthogonal directions provides substantial information about written material, another approach to handwriting analysis is to determine the location of the writing instrument tip at any time. FIGS. 8 and 9 illustrate a handwriting analyzing apparatus which can indicate the location of the writing instrument tip at any instant. Basically, this is accomplished by taking advantage of the fact that, when a writing instrument applies a force to the platen, the beam nearest to the writing instrument bends more than the corresponding beam which is furthest away. The apparatus includes a writing sensor 20A similar to that of FIG. 2, but with additional strain gauges 111, 112, 113, and 114 attached to the inner beams 30, 32 at the top and bottom faces thereof. This apparatus enables the determination of the location of a point 120 at which a writing instrument applies forces. The location of the point 120 is specified by the distance $D_x$ of the point from the laterally-extending line 94 which lies halfway between the ends of the platen 18, and by the distance $D_y$ of the point from another imaginary line 122 that extends longitudinally from the platen halfway between the opposite sides thereof. A determination of these distances is made by an analyzing circuit 124 which is connected to the strain gauges 71–74 on the faces of the outer beams and the strain gauges 111–114 on the faces of the inner beams.

FIG. 9 illustrates a circuit portion 130 for deriving the distance $D_x$, by use of the four strain gauges 71–74 on the outer beams 40, 42 of the writing sensor, but with these strain gauges temporarily connected in a different arrangement. In this balancing circuit, the strain gauges 71–74 are arranged so that the effect of the torques is included instead of balanced out as in the circuit of FIG. 4. The balancing circuit of FIG. 9 includes an amplifier 132 whose output is proportional to the downward force Z applied at the point 120, and multiplied by the moment arm $D_x$ of that force from the center line 94 of the platen. A dividing circuit 134 divides this torque $(Z)(D_x)$ by the force Z to provide an output 136 representing $D_x$. The force Z is determined by the portion of the circuit of FIG. 4 whose output line 109 represents the downward force. Another similar circuit portion 140 provides an output 142 proportional to the distance $D_y$ of the point 120 from the longitudinal center line 122 of the platen. The information about the location of the tip of the writing instrument is especially useful in systems designed to identify the particular characters which are written. Of course, the location of the writing instrument tip can be compared with the downward force Z in signature verification, instead of comparing the downward force Z (and/or any X or Y forces) with a clock output. Instead of utilizing two sets of strain gauges 71–74 and 111–114, it is possible to employ only one set and switch their interconnection to alternately derive three parameters Z, or $(Z)(D_x)$ or $(Z)(D_y)$.

Figure 10:
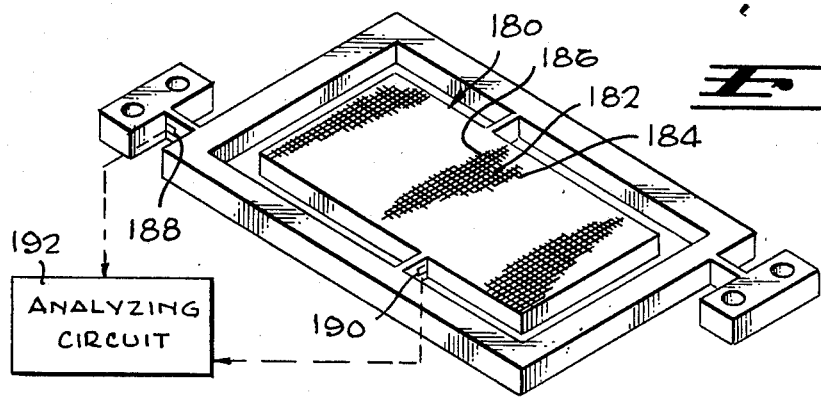
FIG. 10 is a perspective top view of a handwriting analyzing apparatus constructed in accordance with another embodiment of the invention.

FIG. 10 illustrates another embodiment of the invention, wherein a platen 180 is utilized which has a fine grid structure 182 formed thereon, with lines of discontinuity 184 and 186 respectively extending in the X and Y directions. In addition to sensors placed in the manner indicated in FIG. 2, additional sensors 188, 190 are provided to sense the writing instrument crossing the grid lines 184, 186. Each crossing of a grid line results in a sudden change of resistance, or pulse output, of a sensor. Each sensor 188, 190 is connected to an analyzing circuit 192. The circuit 192 can include an up-down counter coupled to each sensor, to indicate the distance of movement of the writing instrument tip in the X and Y directions. The lines of discontinuity 184, 186 in the otherwise smooth surface of the platen, can be formed as grooves or as raised lines.

Thus, the invention provides a compact writing analyzing apparatus, by employing a writing sensor with a platen that has a writing surface extending in a substantially horizontal plane, at least one bending beam extending in substantially the same plane from a location on the platen to support it, and a gauge for measuring bending of the beam. The inner beams which extend from the platen can be connected by an intermediate structure which is, in turn, supported by outer beams that extend perpendicular to the inner beams but in substantially the same, largely horizontal, plane. Gauges attached to the inner and outer beams permit more detailed sensing of forces applied by the tip of a writing instrument. Strain gauges applied to the sides of the inner and outer beams permit measurement of forces in the X and Y horizontal directions. Strain gauges applied to the faces of the beams can be utilized to measure downward forces applied by the pen, or in other words forces in the vertical or Z direction. By utilizing strain gauges on the faces of both the inner and outer beams, measurements can be made of the location of the writing instrument tip at any instant. Of course, a variety of different gauges can be utilized, although strain gauges are among the simplest. Any of the structures can be constructed in an economical manner as by machining the platen, intermediate structure, and connecting beams from a single block of metal, and the entire sensor arrangement is compact and rugged.

Although particular embodiments of the invention have been described and illustrated herein, it is recognized that modifications and variations may readily occur to those skilled in the art and consequently it is intended that the claims be interpreted to cover such modifications and equivalents.

What is claimed is:

1. Apparatus for sensing handwritten markings, comprising:
   a frame;
   a platen having a primarily horizontally-extending support surface for supporting forces produced by the tip of a writing instrument;

beam means including at least one beam having a first end connected to said platen and a second end;

means for coupling said second end of said beam to said frame; and gauge means coupled to said beam, to sense deflection thereof;

said beam extending in substantially the same plane as said platen between said platen and said coupling means.

2. The apparatus described in claim 1 wherein:

said platen is elongated, with side edges extending along the platen length, and with end edges which are shorter than said side edges;

said beam means includes a pair of beams, each beam having a first end connected to one of said side edges and a second end connected to said coupling means; and the first ends of said beams are located at positions spaced in opposite directions from an imaginary line which extends laterally across the width of the platen at a location halfway between the opposite end edges of the platen.

3. The apparatus described in claim 1 wherein:

said coupling means includes a rigid intermediate structure fastened to the first end of said first named beam;

said coupling means also includes outer beam means which comprises an outer beam having a first end connected to said intermediate structure and a second end connected to said frame, and said outer beam extending perpendicular to said first named beam and extending substantially in the plane of said platen; and including second gauge means coupled to said outer beam, to sense deflection thereof.

4. The apparatus described in claim 3 wherein:

said platen and said intermediate structure are formed of a unitary plate of material.

5. The apparatus described in claim 3 wherein:

said beams have top and bottom faces; and said first named and said second gauge means each include a strain gauge fixed to one of said beams at a location halfway between the top face and bottom face of the beam; and including a vertical force sensor including at least one strain gauge fixed to one of the faces of said beams.

6. The apparatus described in claim 3 wherein:

said first named beam means and said outer beam means each includes a pair of beams each having top and bottom faces; and said first named and said second gauge means each include at least four strain gauges, each strain gauge fixed to a face of a different one of said beams; and including circuit means coupled to said strain gauges for generating a first signal which indicates the difference in deflection of said first named beams and for generating a second signal which indicates the difference in deflection of said outer beams, whereby to indicate the location of the writing instrument tip.

7. Apparatus for sensing handwritten markings, comprising:

a plate of resilient material having a plurality of slots extending therethrough forming a central platen region surrounded by an intermediate region extending around said platen region, and also forming a pair of beams connecting said platen and intermediate regions; and gauge means coupled to at least one of said beams to measure deflection thereof.

8. The apparatus described in claim 7 wherein:

said intermediate region includes a rigid structure, and said plate includes a pair of outer beams extending outwardly from said rigid structure, said outer beams extending perpendicular to said first named beams, said plate also including a pair of rigid portions at the outer ends of said outer beams.

9. Apparatus for analyzing handwritten markings comprising:

a platen with an upper face for supporting the forces applied by a writing instrument;

means for supporting said platen with said upper face lying in a primarily horizontal plane, said supporting meas allowing limited movement of said platen along a substantially vertical axis and along two lateral axes that extend perpendicular to one another and to said substantially vertical axis; and means for sensing deflection of said platen along each of said three axes.

10. The apparatus described in claim 9 wherein:

said supporting means includes at least one inner beam extending in substantially the same plane as said platen and having an inner end fixed to said platen and an outer end, a rigid intermediate structure fixed to the outer end of said beam, at least one outer beam extending in substantially the same plane as said platen but perpendicular to said inner beam and having an inner end fixed to said intermediate structure and an outer end, and means for supporting the outer end of said outer beam.

11. Apparatus for sensing handwritten markings, comprising:

a platen having an upper surface with a multiplicity of parallel line discontinuities therein;

means for supporting said platen while allowing limited lateral movement thereof in a predetermined direction perpendicular to the length of said line discontinuities; and means for detecting deflections of said platen in said predetermined direction.

* * * * *